US012016581B2

(12) United States Patent
Sudin et al.

(10) Patent No.: US 12,016,581 B2
(45) Date of Patent: Jun. 25, 2024

(54) WOVEN WIRE INTRALUMINAL DEVICE

(71) Applicant: RAPID MEDICAL LTD., Yokneam (IL)

(72) Inventors: Yuri Sudin, Modiin (IL); Aharon Friedman, Haifa (IL); Ronen Eckhouse, Shimshit (IL); Moshe Miller, Jerusalem (IL)

(73) Assignee: RAPID MEDICAL LTD., Yokneam (IL)

( * ) Notice: Subject to any disclaimer, the term of this patent is extended or adjusted under 35 U.S.C. 154(b) by 340 days.

(21) Appl. No.: 16/345,463

(22) PCT Filed: Oct. 27, 2017

(86) PCT No.: PCT/IB2017/001487
§ 371 (c)(1),
(2) Date: Apr. 26, 2019

(87) PCT Pub. No.: WO2018/078452
PCT Pub. Date: May 3, 2018

(65) Prior Publication Data
US 2019/0269425 A1 Sep. 5, 2019

Related U.S. Application Data

(60) Provisional application No. 62/413,577, filed on Oct. 27, 2016.

(51) Int. Cl.
*A61B 17/221* (2006.01)
*A61B 17/22* (2006.01)
*A61F 2/01* (2006.01)

(52) U.S. Cl.
CPC ...... *A61B 17/221* (2013.01); *A61B 17/22031* (2013.01); *A61F 2002/016* (2013.01);
(Continued)

(58) Field of Classification Search
CPC ............ A61B 17/221; A61B 17/22031; A61B 2017/22034; A61B 2017/0042;
(Continued)

(56) References Cited

U.S. PATENT DOCUMENTS

2002/0169474 A1 11/2002 Kusleika et al.
2004/0153117 A1 8/2004 Clubb et al.
(Continued)

FOREIGN PATENT DOCUMENTS

CN 101088472 A1 12/2007
CN 103841905 A 6/2014
(Continued)

OTHER PUBLICATIONS

WO 2011/032720 A1 Foriegn Translation , Mar. 2011.*
(Continued)

*Primary Examiner* — Ashley L Fishback
*Assistant Examiner* — Chima U Igboko
(74) *Attorney, Agent, or Firm* — FINNEGAN, HENDERSON, FARABOW, GARRETT & DUNNER LLP

(57) ABSTRACT

An intraluminal device including an elongated structure formed of a plurality of wires may be provided. The intraluminal device may include a plurality of sets of looped wires longitudinally located at an intermediate area of the elongated structure. The sets of looped wires may be spaced circumferentially about the elongated structure and may be configured to cooperate with each other to form a plurality of clot entry openings. The intraluminal device may also include at least one grouping of woven wires that may be longitudinally located adjacent to the intermediate area and may be configured such that when an opening force is exerted on the elongated structure, the at least one grouping
(Continued)

of woven wires may provide structural support to hold open first interstices between the plurality of sets of looped wires.

7 Claims, 20 Drawing Sheets

(52) U.S. Cl.
CPC ............... *A61F 2250/0023* (2013.01); *A61F 2250/0039* (2013.01)

(58) Field of Classification Search
CPC .. A61B 2017/22094; A61F 2/013; A61F 2/01; A61F 2002/016; A61F 2230/0097; A61F 2250/0039; A61F 2250/0023
See application file for complete search history.

(56) References Cited

U.S. PATENT DOCUMENTS

| | | | |
|---|---|---|---|
| 2007/0049964 A1 | 3/2007 | Dunfee et al. | |
| 2007/0135834 A1 | 6/2007 | Clubb et al. | |
| 2011/0213403 A1* | 9/2011 | Aboytes | A61M 29/02 606/194 |
| 2014/0343663 A1* | 11/2014 | Sudin | A61B 17/12031 623/1.15 |
| 2016/0199204 A1 | 7/2016 | Pung et al. | |

FOREIGN PATENT DOCUMENTS

| | | | |
|---|---|---|---|
| CN | 104168844 A1 | 11/2014 | |
| CN | 104411357 A1 | 3/2015 | |
| CN | 105250058 A | 1/2016 | |
| CN | 205433998 U | 8/2016 | |
| DE | 10 2009 042 121 B3 | 4/2011 | |
| DE | 10 2009 042121 B3 | 4/2011 | |
| EP | 1576937 A2 | 9/2005 | |
| EP | 2713909 A1 * | 4/2014 | ............ A61B 17/22 |
| JP | WO 2011/151911 A1 | 7/2013 | |
| JP | 2015-504735 A | 2/2015 | |
| WO | WO 2011/032720 A1 | 3/2011 | |
| WO | WO-2011032720 A1 * | 3/2011 | ............ A61F 2/90 |
| WO | WO 2014/081077 A1 | 5/2014 | |
| WO | WO 2016/125018 A2 | 8/2016 | |
| WO | WO 2017/077393 A1 | 5/2017 | |
| WO | WO 2017/103686 A2 | 6/2017 | |
| WO | WO 2017/161204 A1 | 9/2017 | |

OTHER PUBLICATIONS

International Search Report for International Application No. PCT/IB2017/001487, dated Mar. 16, 2018 (2 pages).
Written Opinion of the International Searching Authority for International Application No. PCT/IB2017/001487, dated Mar. 16, 2018 (6 pages).
Extended European Search Report from the European Patent Office for counterpart European Application No. 17865689, dated Apr. 24, 2020 (7 pages).
Japanese Office Action in Japanese Application No. 2019-522446 dated Sep. 8, 2021 (6 pages).
Chinese Office Action in Chinese Application No. 201780066373.0 dated Dec. 3, 2021 (5 pages).
Examination Report No. 1 for counterpart Australian Application No. 2017349575, mailed by IP Australia dated Mar. 24, 2022 (3 pages).

* cited by examiner

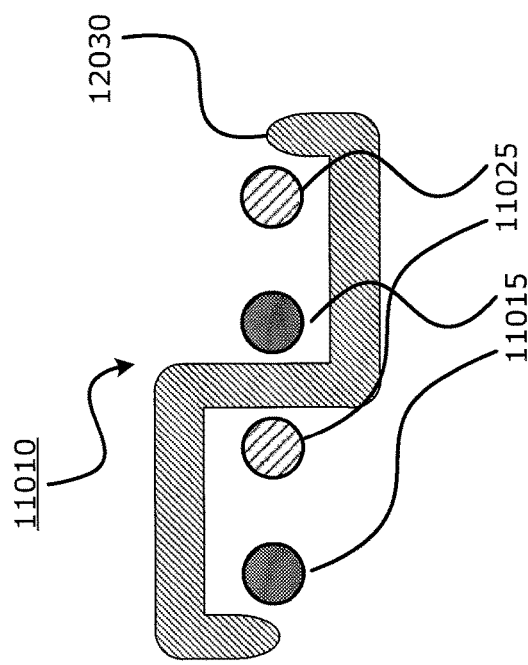
FIG. 13
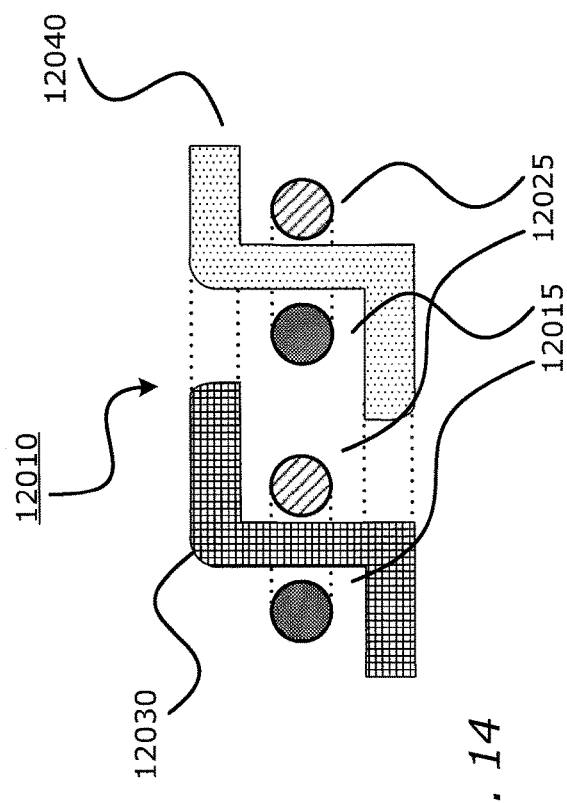
FIG. 14
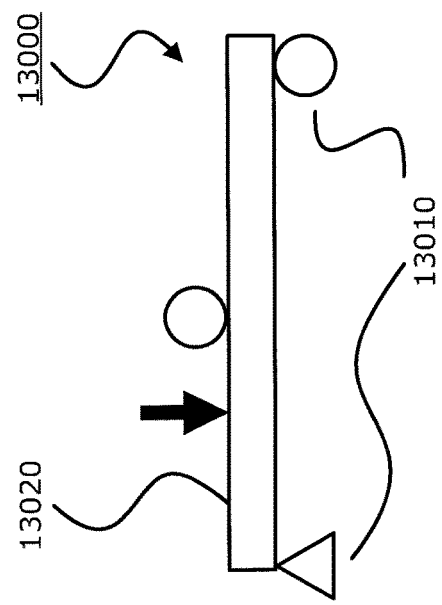
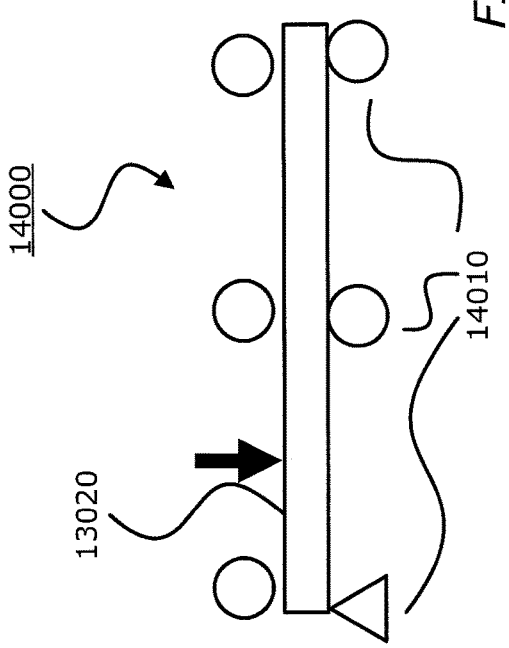

WOVEN WIRE INTRALUMINAL DEVICE

PRIORITY

This application is a U.S. national stage entry under 35 U.S.C. § 371 of International Application No. PCT/IB2017/001487, filed Oct. 27, 2017, which claims the benefit of priority from U.S. Provisional Application No. 62/413,577, filed Oct. 27, 2016, both of which are herein incorporated by reference in their entireties.

FIELD

This disclosure relates to intravascular and/or intraluminal medical devices that are configured to retrieve an obstruction from human blood vessels. Obstructions to be retrieved can include clots and clot material.

SUMMARY

The disclosed embodiments may include an intraluminal device including an elongated structure formed of a plurality of wires. The intraluminal device may include a plurality of sets of looped wires longitudinally located at an intermediate area of the elongated structure. The plurality of sets may be spaced circumferentially about the structure and configured to cooperate with each other to form a plurality of clot entry openings. At least one grouping of woven wires may be longitudinally located adjacent the intermediate area and may be configured such that when an opening force is exerted on the elongated structure, the at least one grouping may provide structural support to hold open first interstices between the plurality of sets of looped wires. In response to the opening force, second interstices may be formed between wires in the at least one grouping of woven wires and the first interstices in the looped wire sets may be larger than the second interstices between wires in each of the at least one grouping.

In another embodiment, at least one grouping of the intraluminal device may include at least two groupings of woven wires, and each grouping may be spaced longitudinally from each other on opposite sides of the intermediate area containing the plurality of sets of looped wires. The at least two groupings of woven wires may cooperate with each other such that when an opening force is exerted on the wire structure, the at least two groupings provide structural support to hold open first interstices between the plurality of sets of looped wires. In response to the opening force, the second interstices may be formed between wires in each of the at least two groupings, and the first interstices in the looped wire sets may be larger than the second interstices between wires in each of the at least two groupings.

In another embodiment, the elongated structure of the intraluminal device may be formed of at least 8 wires, and each of the plurality of sets of looped wires may be formed of the same at least 8 wires as the at least one grouping of woven wires.

In another embodiment, the elongated structure of the intraluminal device may be formed of 12 wires that, in the intermediate area, may define six sets of looped wires. In the adjacent area, the 12 wires may collectively form the at least one grouping of woven wires. In another exemplary embodiment, each of the 12 wires may have a diameter of about 80 microns. In another exemplary embodiment, each wire of the intraluminal device may have a diameter of about 75 microns. By way of another example, each wire of the intraluminal device may have a diameter between 60 and 85 microns. In yet other examples, the wires may be less than 60 microns and greater than 85 microns. In further examples, a single intraluminal device may have wires of varying diameters.

In another embodiment, an intraluminal device may include an elongated structure formed of a plurality of wires. The intraluminal device may include a first region wherein the plurality of wires may be twisted to form a shaft and a second region, adjacent to the first region, wherein the plurality of wires may be woven to form a scaffold. The intraluminal device may also include a third region, adjacent to the second region, wherein the plurality of wires may be separated into sets of looped pairs to form a clot capture structure. The intraluminal device may also include a fourth region wherein the plurality of wires may be braided to form a dense filter configured to catch a blood clot.

In another embodiment, the elongated structure of the intraluminal device may be configured to transition between a collapsed (or retracted) position for delivery to a treatment site, and an expanded position in response to an opening force exerted thereon.

In another embodiment, the elongated structure of the intraluminal device may be configured such that, for example, when the opening force is applied, first interstices may be formed between wires in the second region, and second interstices may be formed between wires in the third region, such that the second interstices are larger than the first interstices.

In another embodiment, the elongated structure of the intraluminal device may be configured such that, for example, when the opening force is applied, third interstices are formed between wires in the fourth region, such that, for example, the third interstices are smaller than both the first interstices and the second interstices.

In another embodiment, the intraluminal device may include a fifth region, adjacent to the fourth region, and wherein the plurality of wires in the fifth region may be twisted to form an additional shaft. In another embodiment, the intraluminal device may include 12 wires and each wire may have a diameter of about 80 microns. In one embodiment, for example, each wire of the intraluminal device may have a diameter of about 75 microns. By way of another example, each wire of the intraluminal device may have a diameter between 60 and 85 microns.

In another embodiment, the elongated structure of the intraluminal device may be configured such that the opening force may be applied through axial movement of the first region. In yet another embodiment, the intraluminal device may include an additional second region of scaffold between the third region and the fourth region.

In another embodiment, an intraluminal device may include an elongated structure formed of a plurality of wires and the device may also include a plurality of cables each formed of a subset of the plurality of wires. The pairs of cables may cross each other at a plurality of intersection locations and at the plurality of intersection locations, wires from each pair of crossing cables may be unwound and woven together with wires from a paired crossing cable. Further, the wires of the crossing cables may be woven together at the intersection locations in a manner permitting the woven-together wires to move relative to each other when an opening force is applied to the elongated structure. Also, in response to the opening force exerted thereon, at the intersection locations, pairs of crossing cables may be configured to pivot relative to each other as the elongated structure transitions between a collapsed (or retracted) position for delivery to a treatment site, and an expanded clot capture position.

BRIEF DESCRIPTION OF THE DRAWINGS

The accompanying drawings, which are incorporated in and constitute a part of this specification, illustrate disclosed embodiments and, together with the description, serve to explain the disclosed embodiments.

FIG. 13 is a cross section view of an exemplary braided structure without twists, and an associated loaded beam diagram;

FIG. 14 is a cross section view of an exemplary braided structure with twists, and an associated loaded beam diagram;

Annotations appearing in the figures are exemplary only, and are not restrictive of the invention as claimed.

DETAILED DESCRIPTION

Reference will now be made in detail to the present embodiments (exemplary embodiments) of the disclosure, examples of which are illustrated in the accompanying drawings. Wherever possible, the same reference numbers will be used throughout the drawings to refer to the same or like parts.

Figure 1:
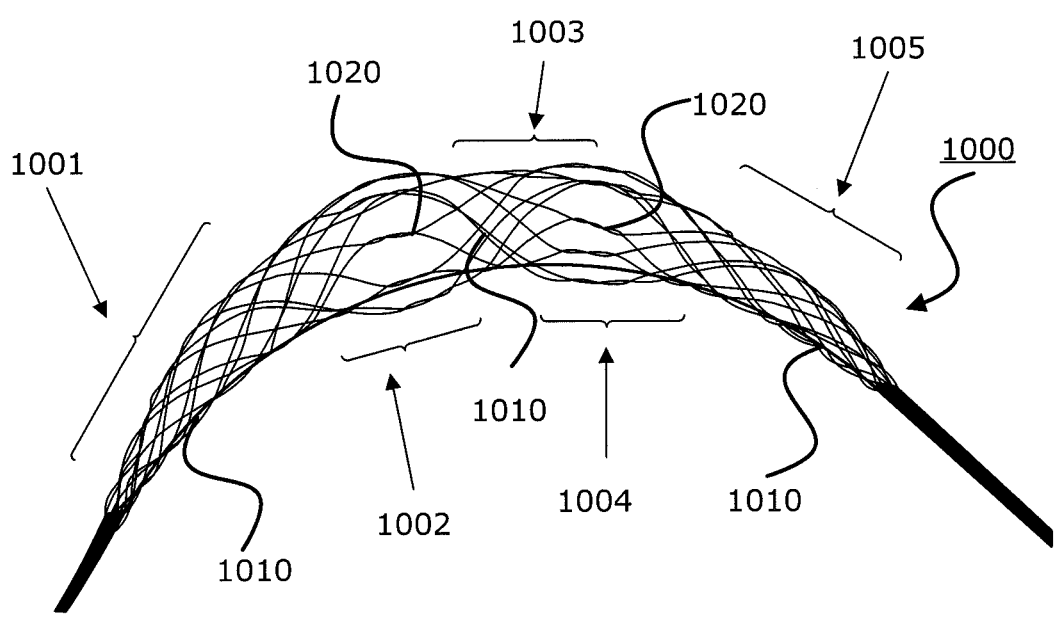
FIG. 1 is an illustration of a first exemplary intraluminal device, consistent with at least one of the disclosed embodiments.
Figure 10:
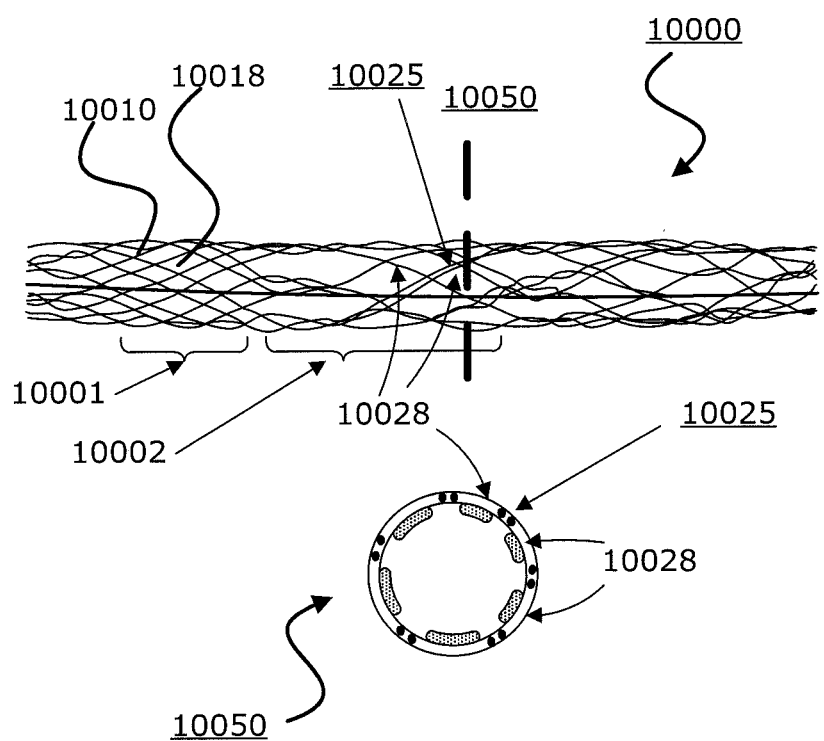
FIG. 10 is a further explanation of the regions of an intraluminal device consistent with at least one of the disclosed embodiments.

FIG. 1 illustrates an exemplary intraluminal device 1000 including five alternating wire zones 1001, 1002, 1003, 1004, and 1005. Zones 1001, 1003 and 1005 include groups of woven wires 1010 and may provide structural support for zones 1002 and 1004. Additionally, since the openings between wires 1010 of zone 1 and 5 may be much smaller they also may provide a distal and proximal filter. (An example of variable sized openings is illustrated in FIG. 10, discussed below.) As a result, clot particles that might appear during the retrieval may be captured at these zones, for example. As further shown in FIG. 1, zones 1002 and 1004 may be constructed of looped wires 1020 to allow a large clot capturing area. And also shown in FIG. 1, zones 1001, 1003, and 1005 may be constructed by woven wires 1010. The number of zones illustrated are exemplary. More or less zones may be provided.

Figure 2:
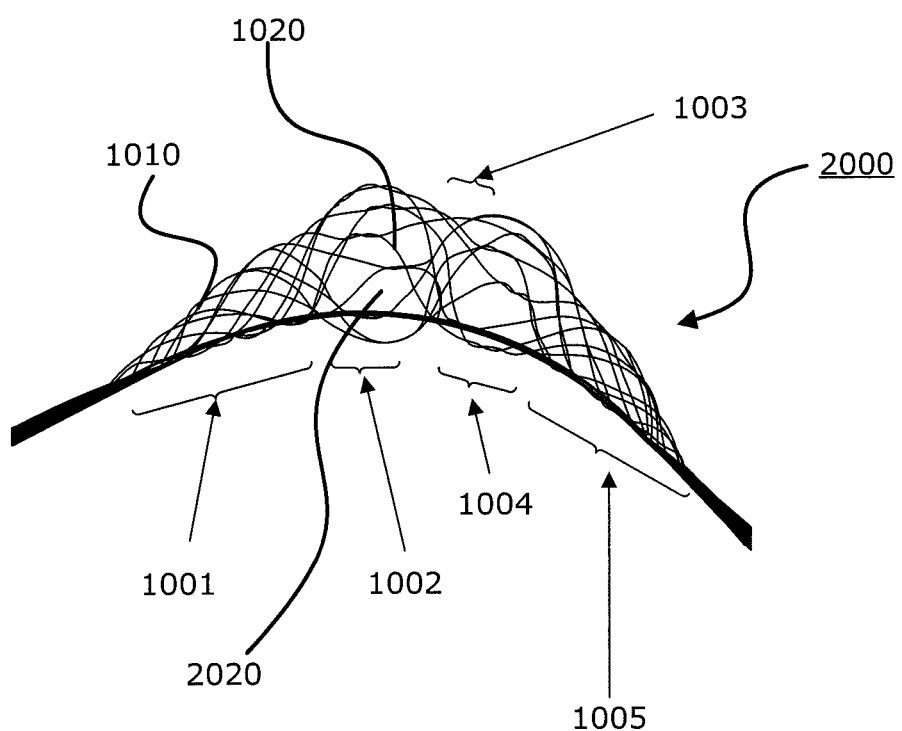
FIG. 2 is an illustration of a second exemplary intraluminal device in accordance with at least one of the disclosed embodiments.

FIG. 2 illustrates an intraluminal device 2000 in a more open position than illustrated in FIG. 1, highlighting the clot entry cells 2020 that may be made from the looped wires 1020. As further shown in FIG. 2, zones 1002 and 1004 may be constructed of looped wires 1020 to allow a large clot capturing area.

Figure 3:
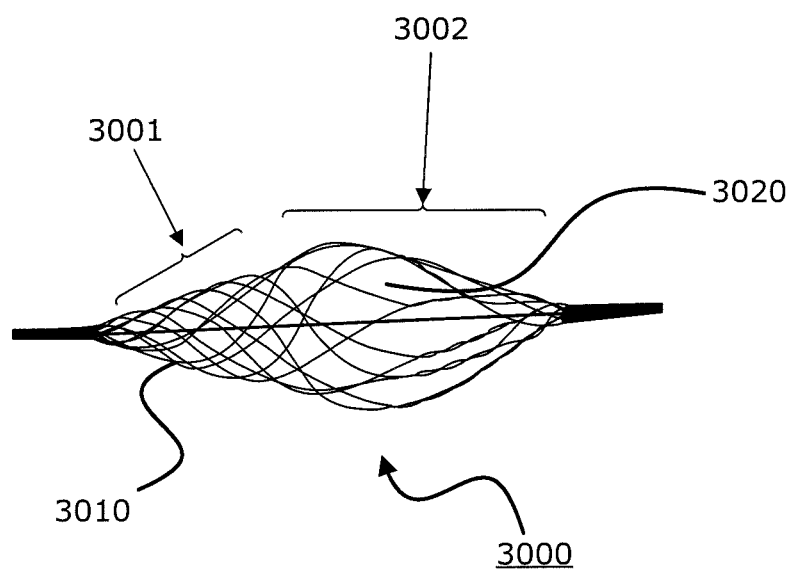
FIG. 3 is an illustration of a third exemplary intraluminal device in accordance with at least one of the disclosed embodiments.

FIG. 3 illustrates yet another exemplary intraluminal device 3000. In this example, as shown in FIG. 3, the device 3000 may be configured so as to include only two different zones. Zone 3001 may be constructed from a group of woven wires 3010, such as for example, densely braided, which provides structural support for the device 3000. In addition, zone 3001 may also serve as a distal filter that prevents emboli from the distal vasculature. As also shown in FIG. 3, zone 3002 may be constructed from wires which are looped which are longitudinally located and provide the clot entry zone 3020. Additionally, zone 3001 may, for example, give structural support and may also serve as a distal filter. As further shown in FIG. 3, zone 3002 may be the clot entering zone.

Figure 4:
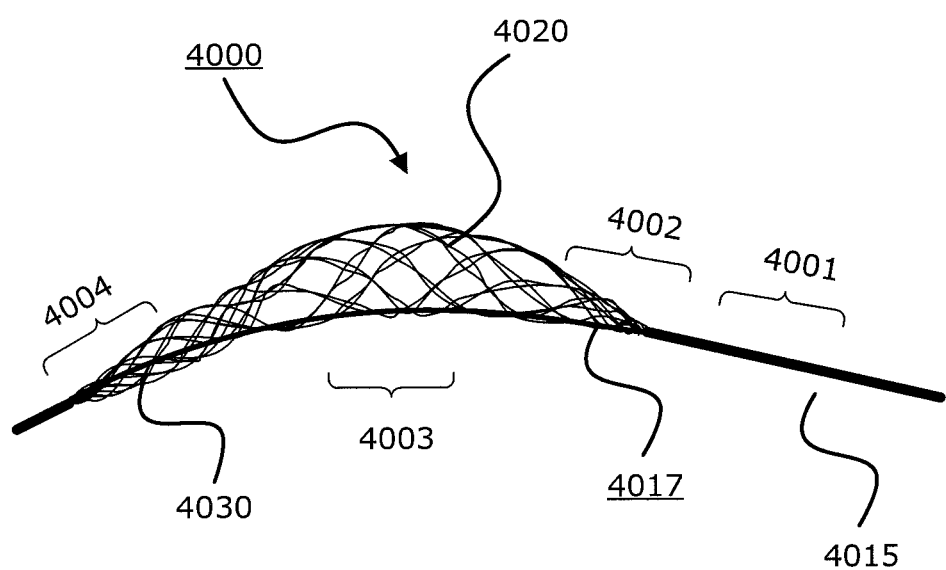
FIG. 4 is an illustration of a fourth exemplary intraluminal device in accordance with at least one of the disclosed embodiments.

FIG. 4 illustrates yet another exemplary intraluminal device 4000 with four regions. In the first region 4001, the wires may be twisted or coiled to form a shaft 4015. In the second region 4002, the wires may be woven to from a scaffold 4017 that supports the opening of the third region 4003. In the third region 4003, the wires may be woven set in looped pairs to form a clot capture structure 4020. For example, the wires of the third region 4003 may be loosely looped or loosely coupled. Further, the fourth region 4004 may be woven to form a distal filter 4030 that captures distal emboli or clot particles. The fourth region 4004 may also serve as a scaffold for the third region 4003.

Figure 5:
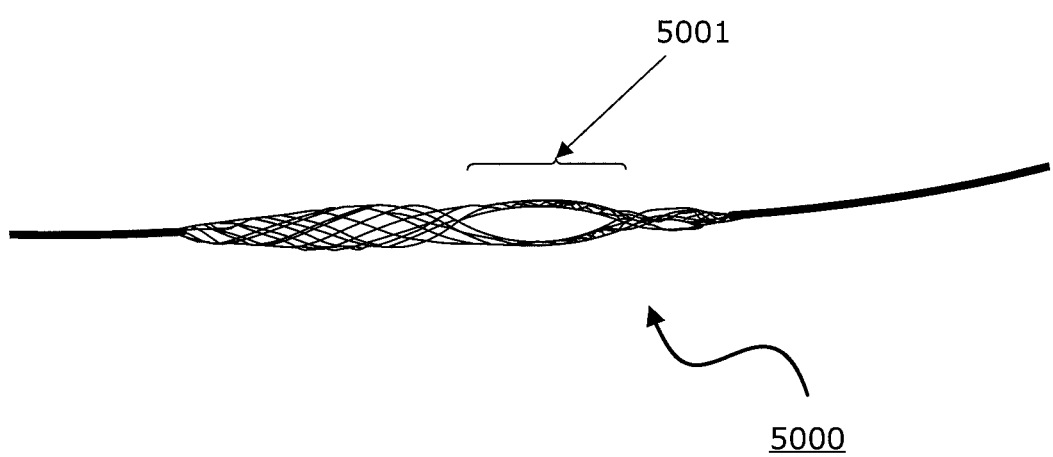
FIG. 5 is an illustration of a fifth exemplary intraluminal device in accordance with at least one of the disclosed embodiments.

FIG. 5 illustrates yet another exemplary intraluminal device 5000. For example, as shown in FIG. 5, the clot opening region 5001 may be woven from three wires that are looped together. Further, the number of wires that are looped together may be greater than two.

Figure 6:
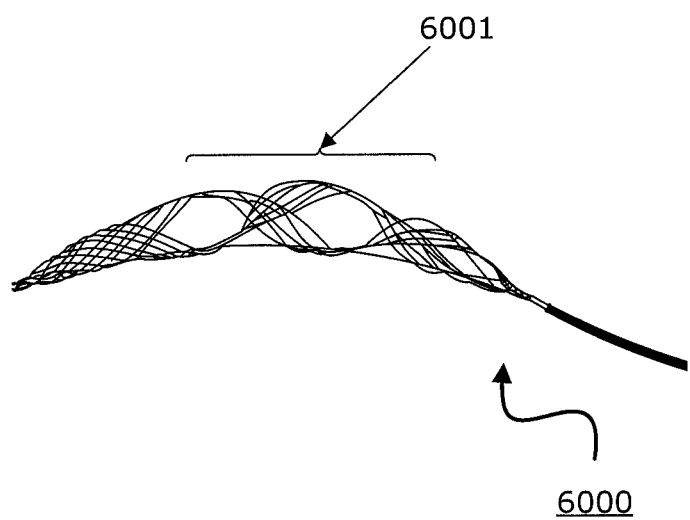
FIG. 6 is an illustration of a sixth exemplary intraluminal device in accordance with at least one of the disclosed embodiments.

FIG. 6 is illustrates yet another exemplary intraluminal device 6000. For example, as shown in FIG. 6, the clot opening region 6001 may be woven from three wires that are loosely looped together. Further, the number of wires that are looped together may be greater than two.

Figure 7:
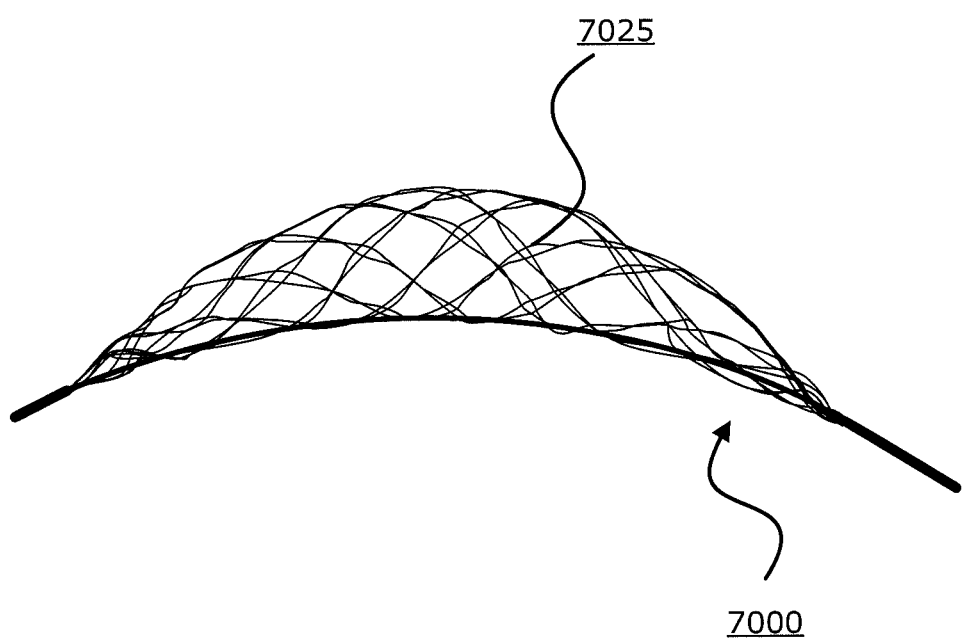
FIG. 7 is an illustration of a seventh exemplary intraluminal device in accordance with at least one of the disclosed embodiments.

FIG. 7 illustrates yet another exemplary intraluminal device 7000. For example, as shown in FIG. 7, the device 7000 may include six cables 7025, in which each cable 7025 may include paired wires. This may create a strong but flexible crossing. And this may further allow, for example, the device 7000 to achieve a flexible structure with a high radial force.

Figure 8:
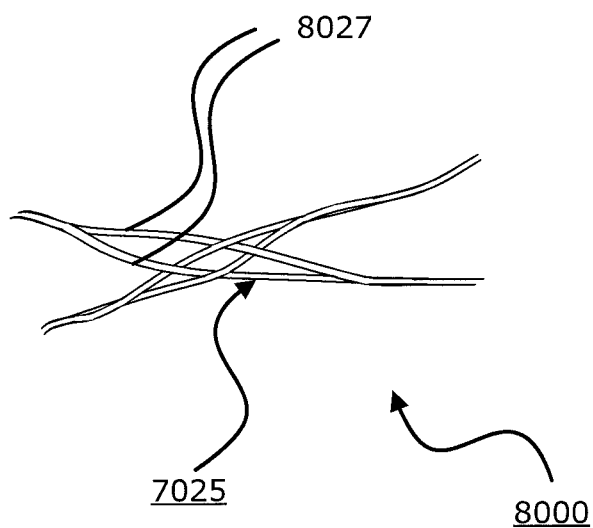
FIG. 8 is an illustration of exemplary cable interweaving, such as is disclosed in connection with FIG. 7.

FIG. 8 illustrates an example of cable interweaving 8000, as discussed above. Each cable 7025, for example, may be made from a looped pair of wires 8027 that are woven with a pair of wires 8027 from a crossing cable. As a result, for example, a semi-flexible and strong crossing point may be achieved.

Figures 9A, 9B:
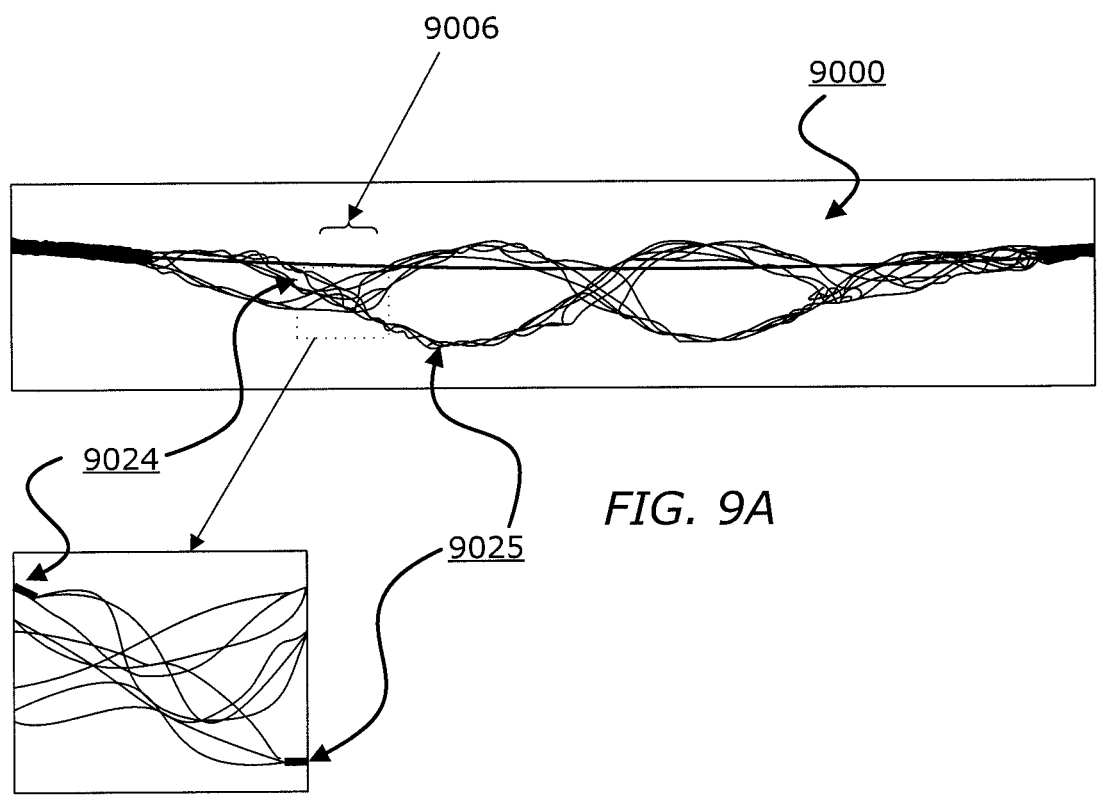
FIG. 9A is an illustration of another exemplary intraluminal device in accordance with at least one of the disclosed embodiments.
FIG. 9B is an enlarged view of a portion of the exemplary intraluminal device shown in FIG. 9A.

FIGS. 9A-9B illustrate yet another exemplary intraluminal device. As shown in FIG. 9A, the cables, for example, may be made from three wires that are unwound and then woven together with the wires from the crossing cable. FIG. 9B also illustrates the cable crossing point 9006 where the cables (including cables 9024 and 9025) are unwound and woven back together. As discussed below in connection with FIGS. 12 and 19C, the braiding structure of FIG. 9A may include a 12-wire braiding structure with a twist before and after each junction frame.

As discussed above in connection with FIG. 1, FIG. 10 illustrates device 10000 with variable-sized openings. Region 10001 includes groups of woven wires 10010 adjacent to intermediate location 10002, and may provide structural support for intermediate location 10002. Specifically, the groupings of woven wires 10010 in region 10001 can provide the support to hold open the first interstices 10028. The first interstices 10028 are larger than the second interstices 10018, where the second interstices are present in region 10001. Cross section 10050 depicts how the cables 10025 are circumferentially displaced in the intermediate location 10002. (The lines making up the ring depicted in cross section 10050 are to indicate the generally circumferential displacement of the cables 10025 about a central region. Moreover, the dotted regions depicted in the cross section 10050 internal to the first interstices 10028 are used to depict the relatively large openings provided for clot entry in the intermediate location 10002.

In accordance with embodiments consistent with the present disclosure, the exemplary intraluminal device may include, for example, two braiding mechanisms, configurations, or structures which may help increase the performance of the device relative to a device incorporating standard braiding structures.

Figure 11:
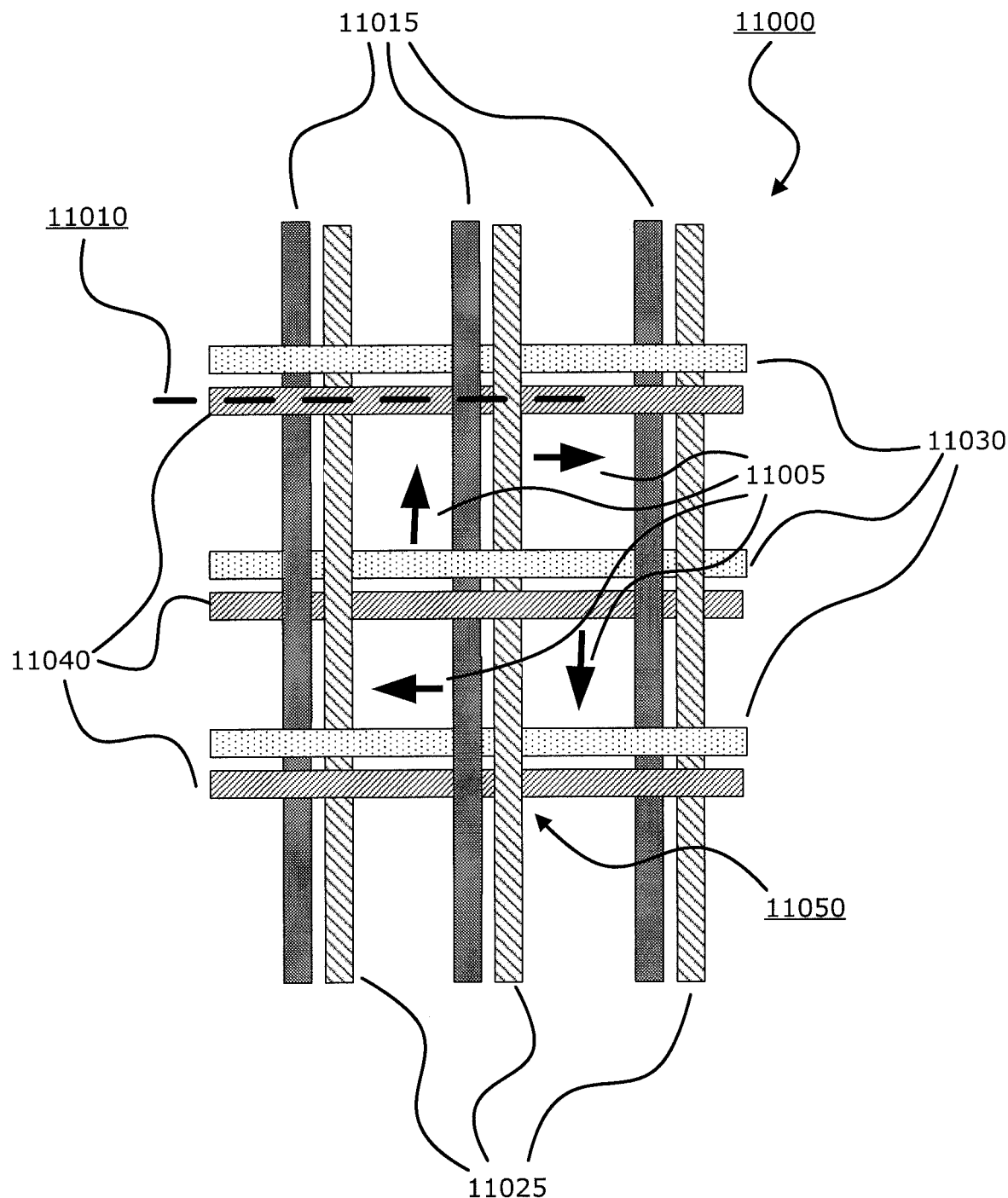
FIG. 11 is an illustration of a braid structure of an exemplary intraluminal device.
Figure 12:
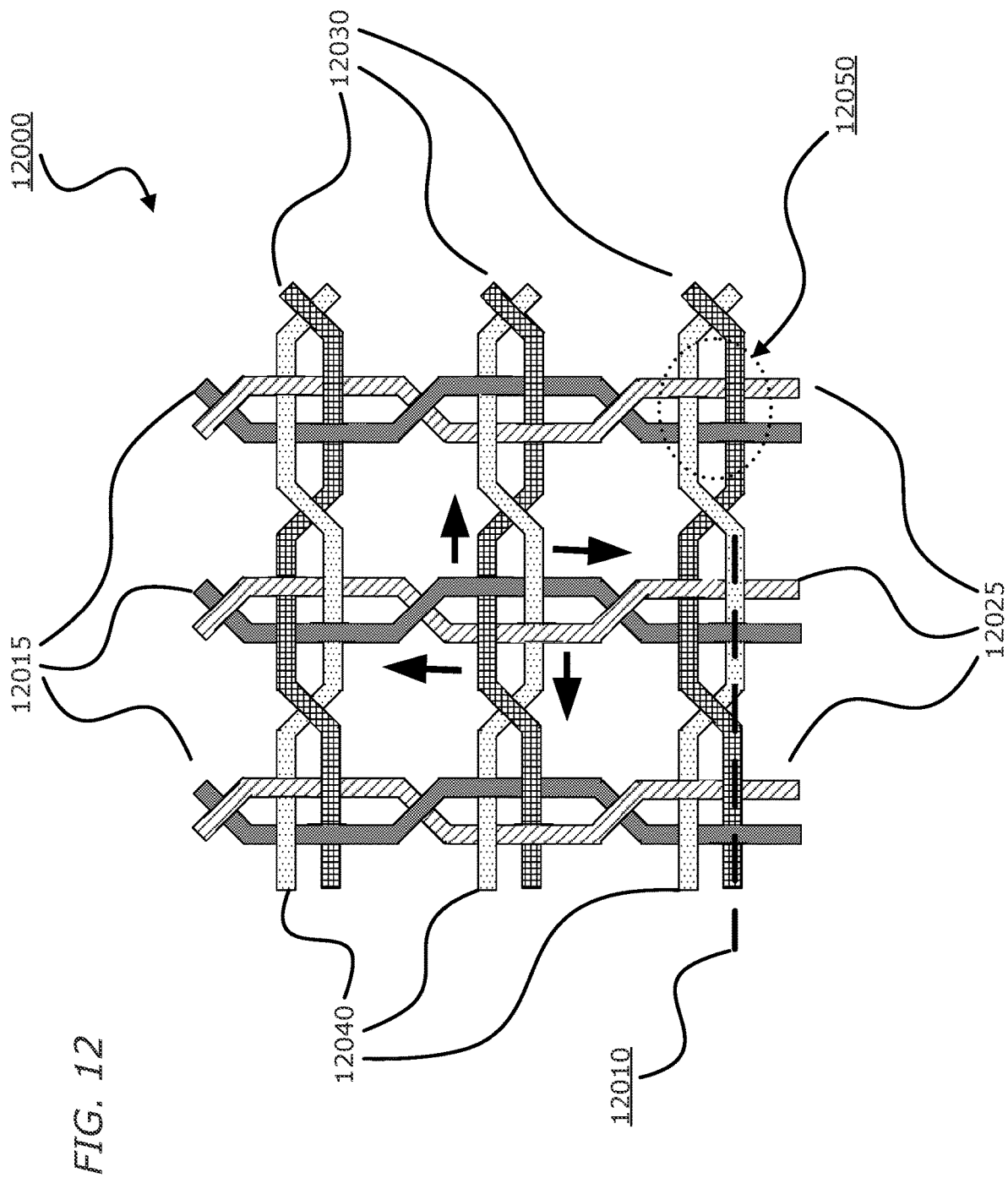
FIG. 12 is an illustration of a braid structure of an exemplary intraluminal device in accordance with at least one of the disclosed embodiments.

For example, as shown in FIG. 12, in accordance with at least some embodiments of an intraluminal device consistent with the present disclosure, the braiding structure 12000 may include a twist of wires before and after each junction frame 12050. Braiding structure 12000 includes three strands of two-wire pairs (two wires 12015 and 12025) braided with three stands of two-wire pairs (two wires 12030 and 12040). FIG. 12 depicts a total of nine (9) junction frames. The junction position within the mesh structure may help prevent slipping of wires across the twist which may otherwise work to become homogeneously separated on a circumference of a mesh structure of an intraluminal device. While a braid structure 11000, as shown in FIG. 11, may enable slippage (illustrated by arrows 11005) until the wire 11040 (for example) reaches a parallel wire 11030, the twists as shown in braiding structure 12000 shown in FIG. 12, may operate to help prohibit substantial slippage across the twist and enable a solid structure when the intraluminal device is expanded.

In accordance with at least some embodiments of an intraluminal device consistent with the present disclosure, and as illustrated in FIGS. 13 and 14, a braiding structure which includes a twist structure may add strength to a mesh structure by operating as a restraint system grasping the wire and dividing an external force applied on the mesh onto additional elements. FIG. 13 depicts cross section 11010 of braiding structure 11000 of FIG. 11 and FIG. 14 depicts cross section 12010 of braiding structure 12000 of FIG. 12. The dotted lines in cross section 12010 of FIG. 14 illustrate a twist in wires 12015 and 12025, and also illustrate a twist in wires 12030 and 12040. The force distribution mechanism in the braiding structures is similar, for example, to force distribution of a loaded beam with varying numbers of supports. This is also illustrated in FIGS. 13 and 14 with the loaded beam diagram 13000 (associated with braided structure 11000) and loaded beam diagram 14000 (associated with braided structure 12000). As illustrated in FIGS. 13 and 14, a loaded beam 13020 with three supports 14010, for example, will react to and distribute the force more effectively than a loaded beam 13020 with two supports 13010, as there is a smaller distance between three supports 14010.

In accordance with at least some embodiments consistent with the present disclosure, the exemplary intraluminal device may be delivered through a microcatheter with an internal diameter of 0.017". As a result, the retriever may have a low profile (in a retracted or compressed state) that is less than that of the internal diameter. In accordance with at least some embodiments of an intraluminal device consistent with the present disclosure, the device may have the five following parts, for example:
 a) a control handle;
 b) a stiff proximal shaft (for example, a stainless steel hypotube);
 c) a flexible shaft (made from a cable of wires, for example);
 d) an expandable mesh which is made from the same wires of the cable; and
 e) a corewire/control wire which may be connected to the distal tip of the mesh and runs through the shafts to the handle.

Figure 19A:
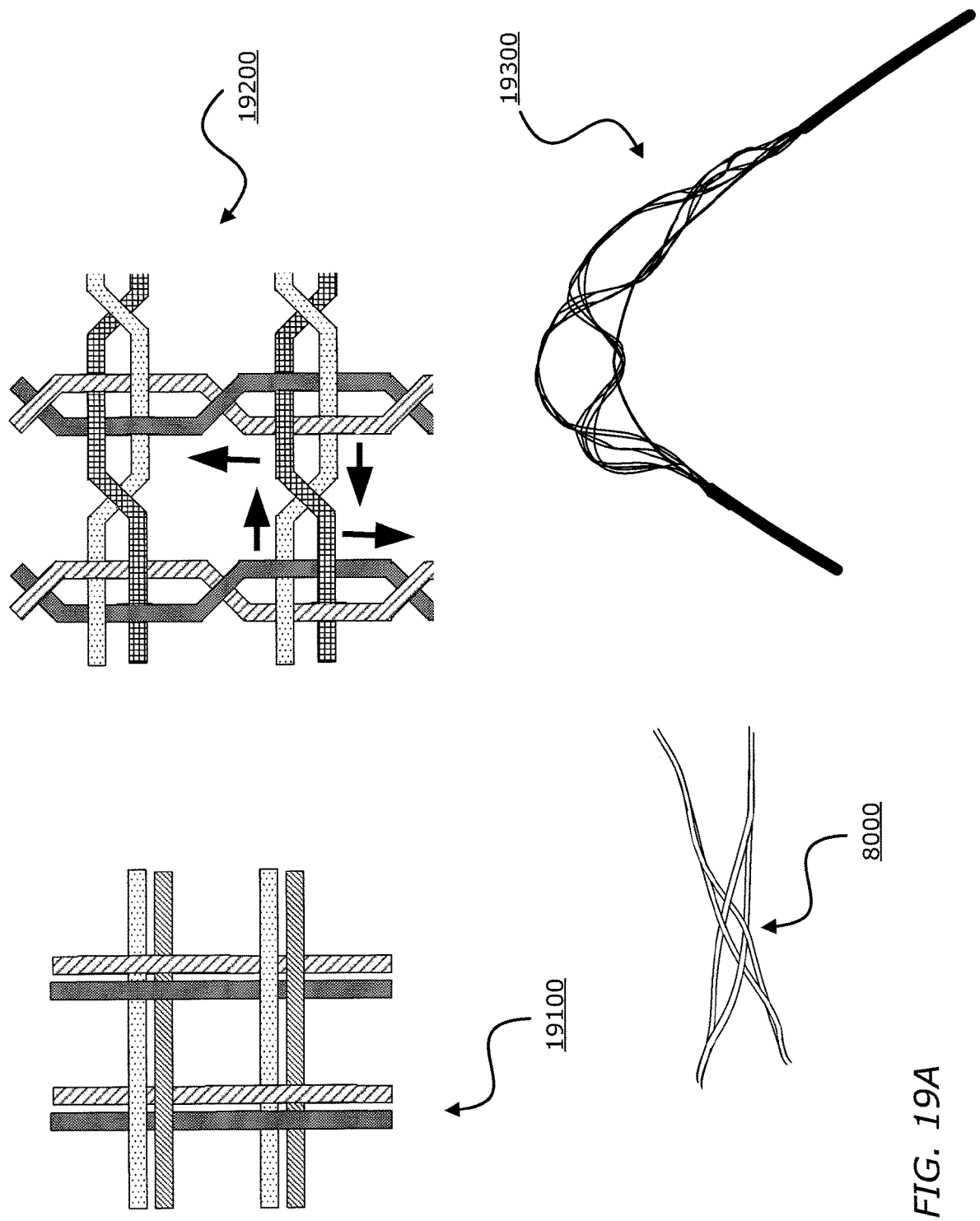
FIGS. 19A-19C illustrate a number of braiding structures consistent with at least some of the disclosed embodiments.

For example, an intraluminal device 19300 (shown in FIG. 9A) may include a flexible shaft with eight (8) wires (each wire having a diameter of 70 μm) and a mesh including eight (8) wires (each wire having a diameter of 70 μm). The eight wires, for example, may be formed, for example, by creating four strands of wires braided together, with each strand including two (2) wires each. As shown in FIG. 19A, and discussed above, the braiding structure 19200 may include a twist of wires before and after each junction frame to help prevent slippage. A detailed view of cable interweaving 8000 (discussed in connection with FIG. 8) is also shown in FIG. 19A. Cable interweaving 8000 illustrates a junction in braiding structure 19200 of device 19300 in detail. The wires may, for example, be made from Nitinol. FIG. 19A also depicts braiding structure 19100 without a twist before and after a junction frame.

Figure 19B:
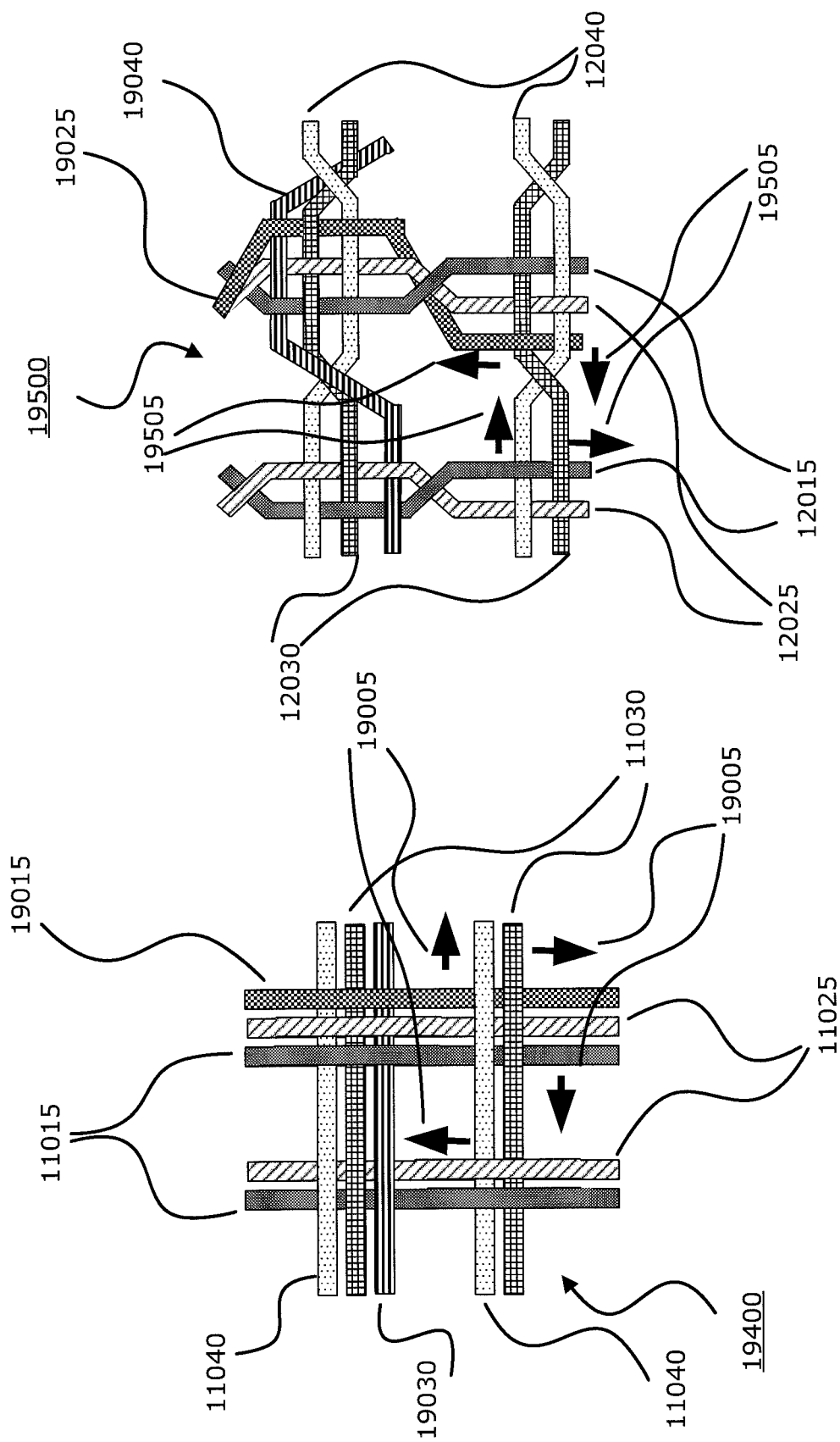
Figure 19C:
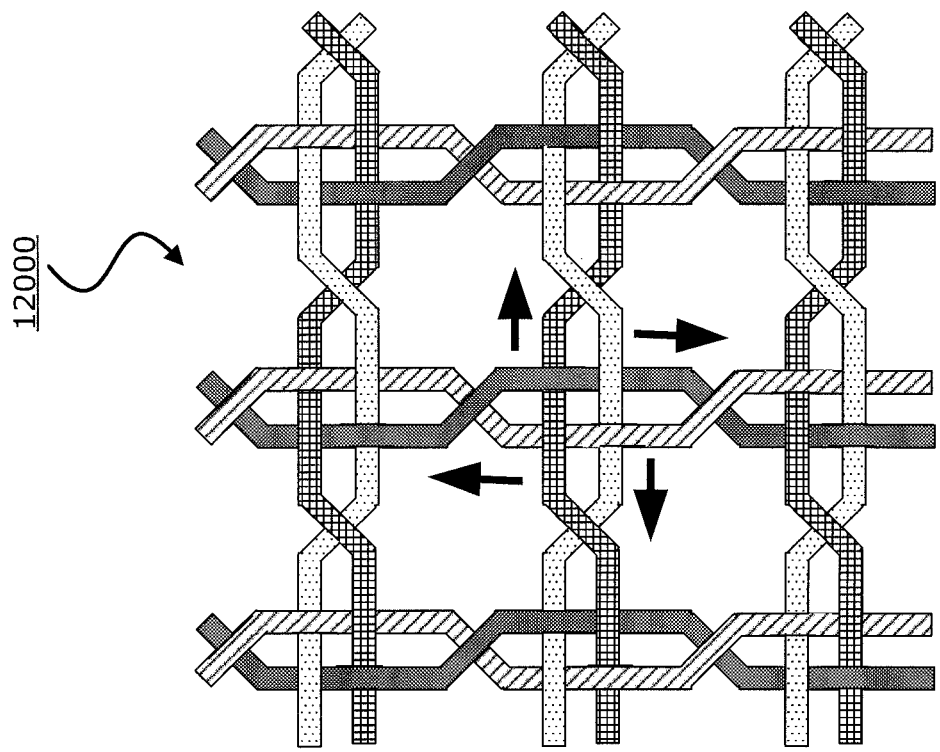
Figure 19C:
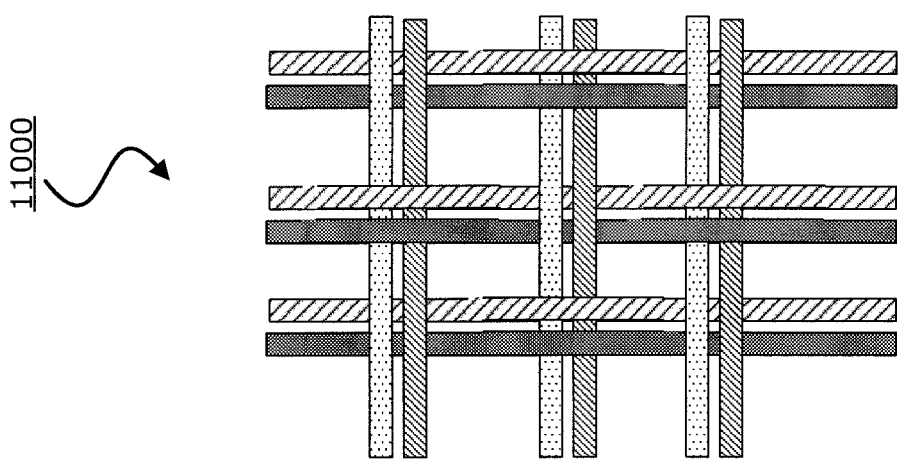

In another exemplary embodiment, the intraluminal device may include a flexible shaft with twelve (12) wires and a mesh including twelve (12) wires. The twelve (12) wires may be formed, for example, by creating six strands of wires braided together: with three strands including two (2) wires each; while the other three strands may include two (2) wires each. As shown in FIG. 19C, and discussed above (such as in connection with FIG. 8, which shows cable interweaving 8000, and FIG. 12, which shows braiding structure 12000), the braiding structure 12000 for this embodiment may include a twist of wires before and after each junction frame to help prevent slippage. FIG. 19C also depicts braiding structure 11000 without a twist before and after a junction frame. An exemplary intraluminal device with twelve (12) wires includes device 9000 of FIG. 9.

Figure 15:
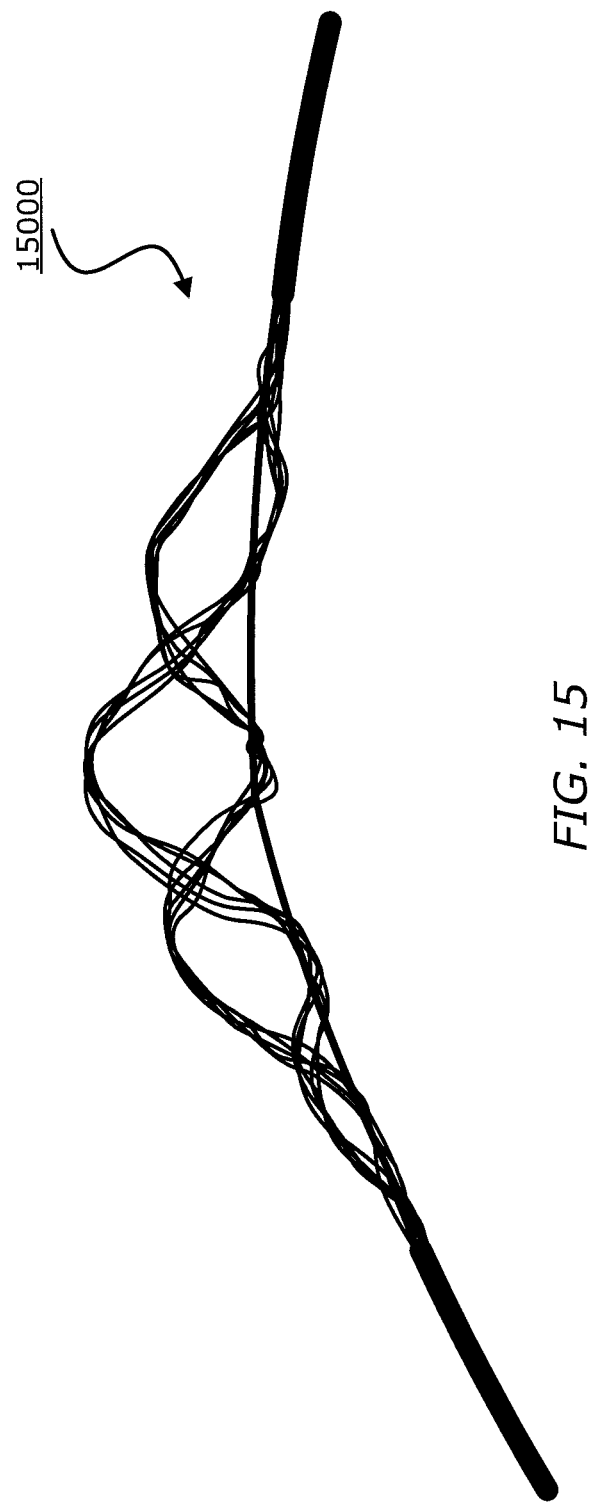
FIG. 15 is an illustration of an exemplary intraluminal device, consistent with at least one of the disclosed embodiments.

In accordance with another embodiment consistent with the present disclosure, the flexible shaft of the exemplary intraluminal device may include a flexible shaft with ten (10) wires and a mesh including ten (10) wires. The ten (10) wires may be formed, for example, by creating four strands of wires braided together: with two strands including three (3) wires each; while the other two strands may include two (2) wires each. Exemplary braiding structures with ten (10) wires are illustrated in FIG. 19B. The braiding structure 19500 may include a twist of wires before and after each junction frame. Braiding structure 19500 includes two-wire strand (wires 12015 and 12025) and three-wire strand (wires 12015, 12025, and 19025) braided with two-wire strand (wires 12030 and 12040) and three-wire strand (12030, 12040, and 19040). Slippage arrows 19505 are also shown. A braiding structure 19400 without a twist is also illustrated. Braiding structure 19400 includes two-wire strand (wires 11015 and 11025) and three-wire strand (wires 11015, 11025, and 19015) braided with two-wire strand (wires 11030 and 11040) and three-wire strand (11030, 11040, and 19030). Slippage arrows 19005 are also shown. In each strand of wires, the wires may, for example, be intertwined to create a stable strand. The wires may, for example, be made from Nitinol, and this configuration may be achieved, for example, by cutting two wires at a transition between a cable and mesh (although this may involve another manufacturing step). As shown in FIG. 15, which represents a general view of an exemplary intraluminal device 15000 in accordance with the present disclosure, the strands may cross each other to create large openings (cells). In the intersections, for example, the strands may be intertwined with one another to create a loosely coupled junction. Before and after the junction, for example, the wires of the strands may be intertwined.

Figure 16:
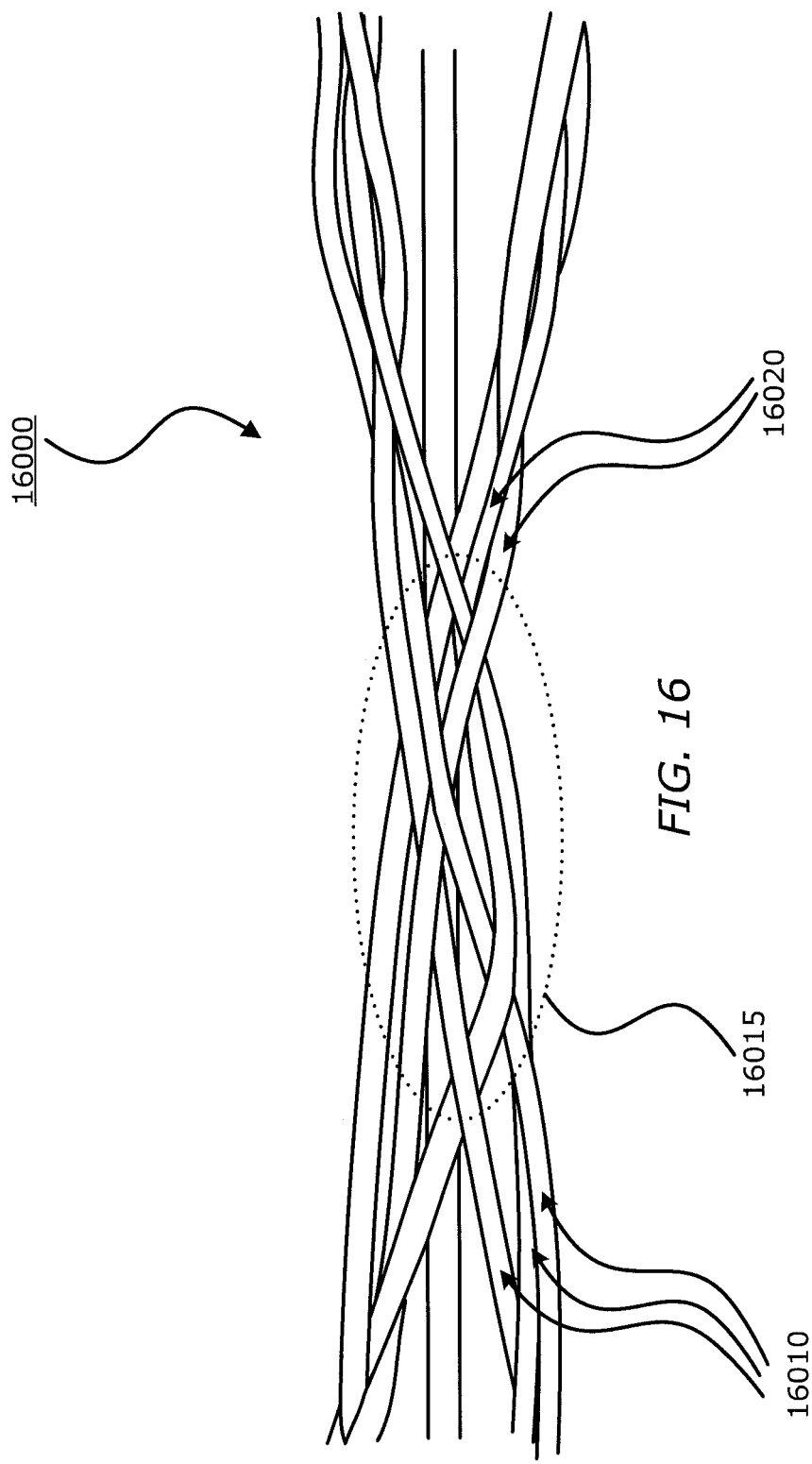
FIG. 16 is an enlarged view of a portion of the exemplary intraluminal device shown in FIG. 15.
Figure 17:
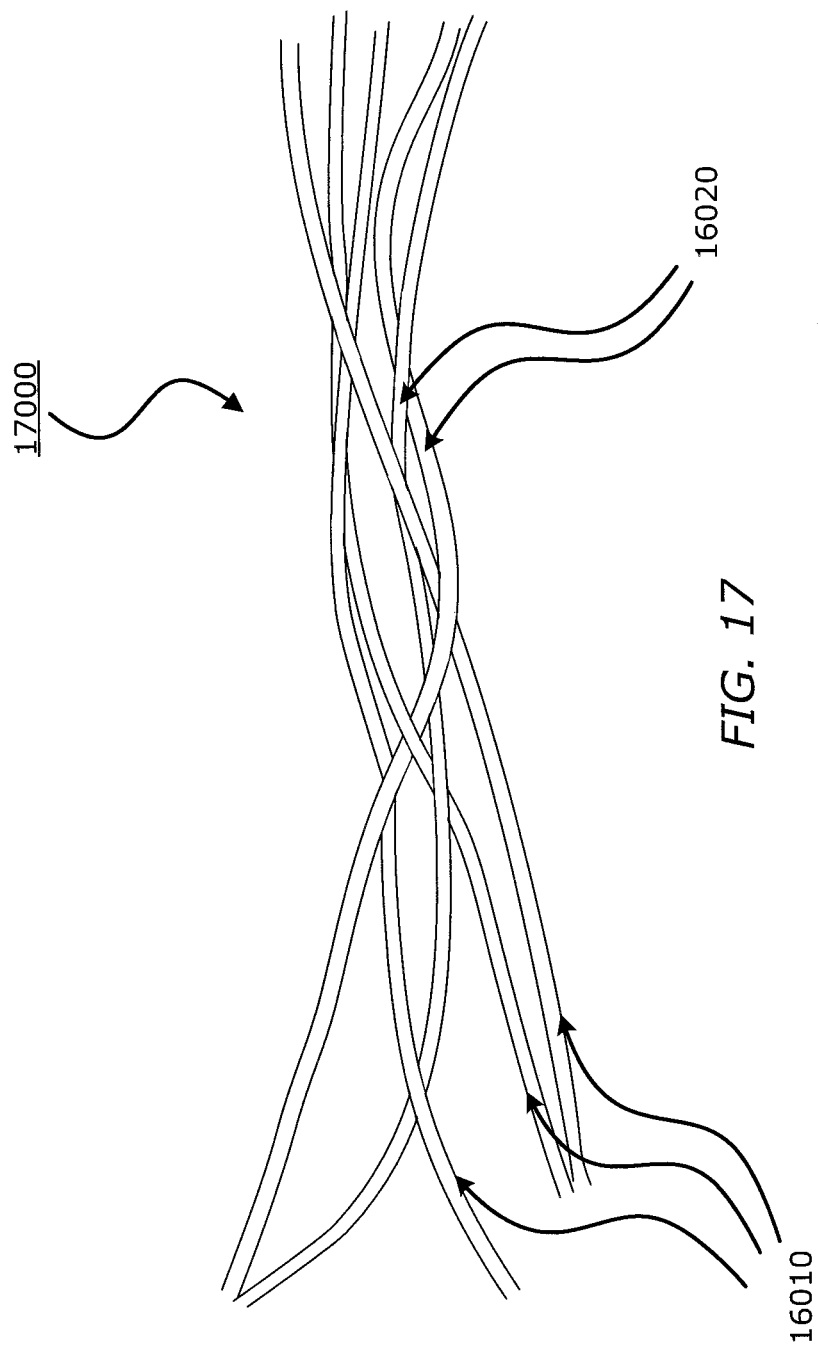
FIG. 17 is an enlarged view of a portion of the exemplary intraluminal device shown in FIG. 15 in an expanded position.
Figure 18:
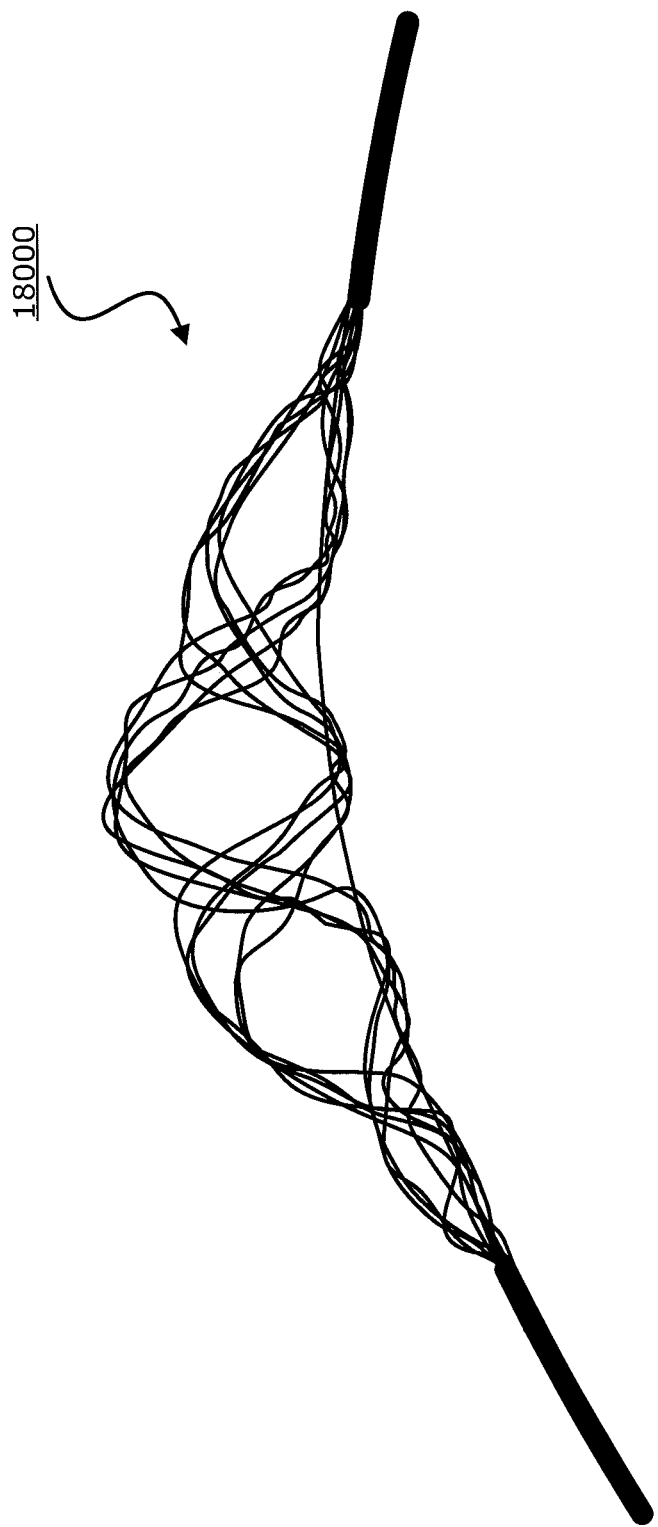
FIG. 18 is an illustration of exemplary intraluminal device in an expanded position in accordance with at least one of the disclosed embodiments.

As shown in FIG. 16, a strand of two wires (i.e., wires 16020) may cross a strand of three wires (i.e., wires 16010). The intertwined wires before and after the junction and the intertwining of the wires inside the junction may create a loosely coupled but stable junction and cross-section, which helps prevent slippage and create large cells, ultimately helping to resist collapse of the device when expanded with high radial force within a tube. And, as shown in FIGS. 17-18 (where FIG. 17 is a detail of region 16015 of FIG. 16 in an expanded configuration, and FIG. 18 is a detail of FIG. 15 in an expanded configuration), when the mesh is expanded, the junction structure keeps the wires together even when the mesh is expanded. As a result, the mesh size remains the same.

FIGS. 19A, 19B, and 19C illustrate, respectively, 8-, 10-, and 12-wire junctions and configurations. In addition, as discussed above, devices 15000 and 18000, and the detailed views of FIGS. 16 and 17 may use the 12-wire junctions of FIG. 19C. Of course, these are only examples, and the wire junctions and configurations with more or less wires may be used, and that regardless of the number of wires, differing braiding arrangements may be employed.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

What is claimed is:

1. An intraluminal device comprising:
an elongated structure formed of a plurality of wires, the elongated structure including a plurality of strands that are intertwined with each other to create a plurality of loosely coupled junctions, each strand comprising a set of two or more wires of the plurality of wires that are looped together, the elongated structure having a proximal end, a distal end opposite from the proximal end, and an intermediate portion extending between the proximal and distal ends;
a clot capturing area longitudinally located within the intermediate portion of the elongated structure, wherein the plurality of strands are spaced circumferentially about the elongated structure and are configured to cooperate with each other to form a plurality of clot entry openings within the clot capturing area, wherein the clot capturing area includes at least two strand configurations or at least two braiding configurations at the plurality of loosely coupled junctions, each junction of the plurality of loosely coupled junctions including a weaving of a first strand and a second strand such that a first wire of the first strand is situated between two wires of the second strand and a second wire of the second strand is situated between two wires of the first strand, and wherein the plurality of strands within the clot capturing area includes a twist of wires before and after each plurality of loosely coupled junctions; and
at least one grouping of woven wires longitudinally located adjacent to the clot capturing area,
wherein the at least one grouping of woven wires is configured such that when an opening force is exerted on the elongated structure, the at least one grouping of woven wires provides structural support to hold open first interstices between the plurality of strands, and
wherein in response to the opening force, second interstices are formed between wires in the at least one grouping of woven wires, the first interstices between the strands being larger than the second interstices between the wires in the at least one grouping of woven wires.

2. The intraluminal device of claim 1,
wherein the at least one grouping of woven wires includes at least two groupings of woven wires, each grouping of woven wires being spaced longitudinally from each other on opposite sides of the clot capturing area containing the plurality of strands,
wherein the at least two groupings of woven wires are configured to cooperate with each other such that when the opening force is exerted on the elongated structure, the at least two groupings of woven wires provide structural support to hold open the first interstices between the plurality of strands, and wherein in response to the opening force, the second interstices are formed between wires in each of the at least two groupings of woven wires, the first interstices between the strands being larger than the second interstices between the wires in the at least two groupings of woven wires.

3. The intraluminal device of claim 1,
wherein the elongated structure is formed of at least twelve wires, and
wherein the at least twelve wires form the plurality of strands and the at least one grouping of woven wires.

4. The intraluminal device of claim 3, wherein the at least twelve wires are arranged in six pairs of strands within the clot capturing area and collectively form the at least one grouping of woven wires.

5. The intraluminal device of claim 1, wherein at least one wire of the plurality of wires has a diameter of between about 75 microns and about 80 microns.

6. The intraluminal device of claim 1,
wherein the elongated structure is formed of at least ten wires,
wherein the at least ten wires form the plurality of strands and the at least one grouping of woven wires, and
wherein at least one wire of the at least ten wires has a diameter of about 70 microns.

7. The intraluminal device of claim 1,
wherein the elongated structure is formed of at least eight wires,
wherein the at least eight wires form the plurality of strands and the at least one grouping of woven wires, and
wherein at least one wire of the at least eight wires has a diameter of about 70 microns.

* * * * *